(12) United States Patent
Tillett

(10) Patent No.: US 6,737,253 B1
(45) Date of Patent: May 18, 2004

(54) METHOD OF AMPLIFICATION OF NUCLEIC ACIDS

(75) Inventor: Daniel Tillett, Randwick (AU)

(73) Assignee: Takara Shuzo Co., Inc., Kyoto (JP)

( * ) Notice: Subject to any disclaimer, the term of this patent is extended or adjusted under 35 U.S.C. 154(b) by 0 days.

(21) Appl. No.: 09/581,822

(22) PCT Filed: May 1, 2000

(86) PCT No.: PCT/AU00/00391
§ 371 (c)(1),
(2), (4) Date: May 20, 2002

(87) PCT Pub. No.: WO00/66768
PCT Pub. Date: Nov. 9, 2000

(30) Foreign Application Priority Data

Apr. 30, 1999 (AU) ............................................. PQ0087

(51) Int. Cl.[7] ........................... C12P 19/34; C07H 21/04
(52) U.S. Cl. .................................... 435/91.2; 536/24.33
(58) Field of Search .................... 435/6, 91.1, 91.2, 435/810; 536/24.33, 24.3; 935/76, 77, 78

(56) References Cited

U.S. PATENT DOCUMENTS

| 5,104,792 A | * | 4/1992 | Silver et al. .................. 435/6 |
| 5,962,228 A | * | 10/1999 | Brener ........................... 435/6 |
| 6,043,059 A | * | 3/2000 | Reeve et al. ............... 435/91.1 |
| 2001/0046681 A1 | * | 11/2001 | Senapathy ..................... 435/6 |

FOREIGN PATENT DOCUMENTS

| EP | 0 757 240 | 4/1997 |
| WO | WO 97/01645 | 1/1997 |

OTHER PUBLICATIONS

Shuber et al., "A Simplified Procedure for Developing Multiplex PCRs" Genome Research, 5:488–493 (1995).*

Liu et al., "Thermal Asymmetric Interlaced PCR: Automatable Amplification and Sequencing of Insert End Fragments from P1 and YAC Clones for Chromosome Walking", Genomics, 25:674–681 (1995).

Waclaw Szybalski, "From the double–helix to novel approaches to the sequencing of large genomes", Gene, 135:279–290 (1993).

Churcher et al., "Sequencing strategies", Chapter 20, 517–527, The Sanger Centre, Wellcome Trust Genome Campus, Hinxton, Cambridge, UK.

Ghiso et al., "A Subset of 1200 Hexamers is Sufficient to Sequence over 95% of cDNAs by Hexamer String Primer Walking", Genomics, 17:798–799 (1993).

* cited by examiner

*Primary Examiner*—Kenneth R. Horlick
(74) *Attorney, Agent, or Firm*—Leydig, Voit & Mayer, Ltd.

(57) ABSTRACT

The present invention relates generally to genetic analysis and, in particular, to genomics. More specifically, the invention relates to a method of amplification of a nucleic acid (or a nucleotide sequence of interest) which may be applied to sequencing in general and, in particular, to genome sequencing.

50 Claims, 6 Drawing Sheets

Fig. 1
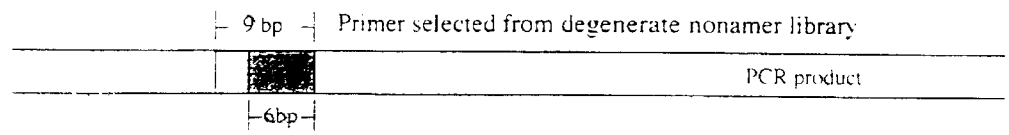
First primer anneals (~40°C) and extends
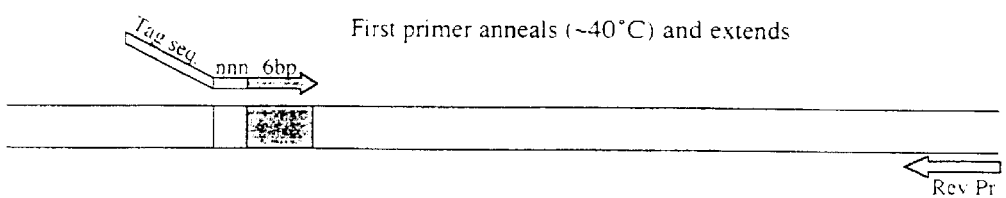
After 2 cycle the tag sequence is introduced into the PCR product.
Second primer can anneal (~55°C)
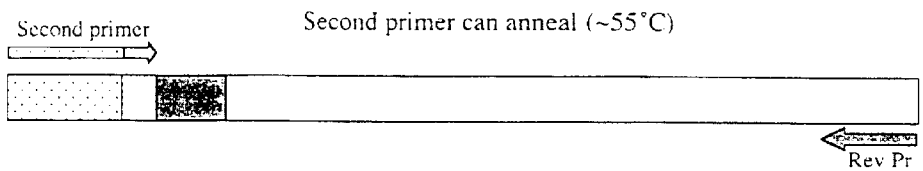
10-25 PCR cycles
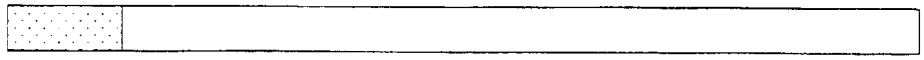
Cycle sequence using tag primer
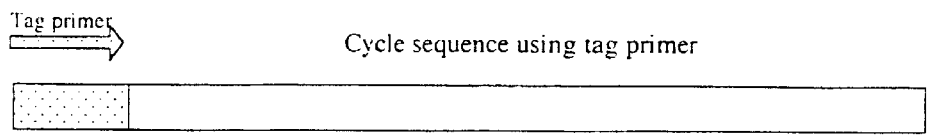

Fig. 3                                                                SEQ ID NO: 1

EK10FS
tttaacccataccagtacaatggctatggtttttacattttacgcaaggggcaattgtgaaactggatgaa
atcgctcggctggcgggagtgtcgcggaccactgcaagctatgttattaacggcaaagcgaagcaataccg
tgtgagcgacaaaaccgttgaaaaagtcatggctgtggtgcgtgagcacaattaccacccgaacgccgtgg
cagctgggcttcgtgctggacgcacacgttctattggtcttgtgatcccgatctggagaacaccagctat
acccgcatcgctaactatcttgaacgccaggcgcggcaacggggttatcaactgctgattgcctgctcaga
agatcagccagacaacgaaatgcggtgcattgagcacctttacagcgtcaggttgatgccattattgttt
cgacgtcgttgcctcctgagcatccttttttatcaacgctgggctaacgaccccgttcccgattgtcgcgctg
gaccgcgccctcgatcgtgaacacttcaccagcgtggttggtgccgatcaggatgatgccgaaatgctggc
ggaagagttacgtaagtttcccgccgagacggtgctttatcttggtgcgctaccggagctttctgtcagct
tcctgcgtgaacaaggtttccgtactgcctggaaagatgatccgcgcgaagtgcatttcctgtatgccaac
agctatgagcgggaggcggctgcccagttattcgaaaaatggctggaaacgcatccgatgccgcaggcgct
gttcacaacgtcgtttgcgttgttgcaaggagtgatggatgtcacgctgcgtcgcgacggcaaactgcctt
ctgacctggcaattgccacctttggcgataacgaactgctcgacttcttacagtgtccggtgctggcagtg
gctcaacgtcaccgcgatgtcgcagagcgtgtgctggagattgtcctggcaagcctggacgaaccgcgtaa
gccaaaacctggtttaacgcgcattaaacgtaatctctatcgccgcggcgtgctcagccgtagctaagccg
cgaacaaaaatacgcgccaggtgaatttccctctggcgcgtagagtacgggactggacatcaatatgctta
aagtaaataagactattcctgactattattgataaatgcttttaaacccgcccgttaattaactcaccagc
tgaaattcacaataattaagtgatatcgacagcgcgttttttgcattattttgttacatgcggcgatgaatt
gccgatttaacaaacacttttctttgcttttgcgcaaacccgctggcatcaagcgccacacagacgtaaca
aggactgttaaccggggaagatatgtcctaaaatgccgctcgcgtcgcaaactgacactttatatttgctg
tggaaaatagtgagtcatttaaaaacggtgatgacgatgagggatttttttcttacagctattcataacgtt
aatttgcttcgcacgttggacgtaaaataaacaacgctgatattagccgtaaacatcgggttttttacctc
ggtatgccttgtgactggcttgacaagcttttcctcagctccgtaaactcctttcagtgggaaattgtggg
gcaaagtgggaataaggggtgaggctggcatgttccggggagcaacgttagtcaatctcgacagcaaaggg
cgcttatcagtgcctacccgtta
        EK10R

Fig. 5

SEQ ID NO: 7

Ggtaccagttgaagtccgtccggttcgtcgtaatgctctggcaatgcgttggatcgttgaagctgctcgt
aaacgcggtgataaatccatggctctgcgcctggcgaacgaacttctgatgctgcagaaaacaaaggta
ctgcagttaagaaacgtgaagacgttcaccgtatggccgaagccaacaaggcgttcgcacactaccgttg
gttatcccttcggagtttttagtcaccaggcgggcgcttccagtaagcagcccgctttgggctacttaaat
tgaacgcctaaaagataaacgaggaaacaaatggctcgtacaacacccatcgcacgctaccgtaacatcg
gtatcagtgcgcacatcgacgccggtaaaaccactactaccgaacgtattctgttctacaccggtgtaaa
                                      4G1
ccataaaatcggtgaagttcatgacg[gcgctgcaa]ccatggactggatggagcaggagcaggaacgtgg
tattaccatcacttccgctgcgactactgcattctggtctggtatggctaagcagtatgagccgcatcgc
atcaacatcatcgacacccggggcacgttgacttcacaatcgaagtagaacgttccatgcgtgttctcg
atggtgcggtaatggtttactgcgcagttggtggtgttcagccgcagtctgaaaccgtatggcgtcaggc
aaacaaatataaagttccgcgcattgcgttcgttaacaaaatggaccgcatgggtgcgaacttcctgaaa
gttgttaaccagatcaaaaccgtctgggcgcgaacccggttccgctgcagctggcgattggtgctgaag
aacatttcaccggtgttgttgacctggtgaaaatgaaagctatcaactggaacgacgctgaccagggcgt
aaccttcgaatacgaagatatcccggtagacatggttgaactggctaacgaatggcaccagaacctgatc
gaatccgcagctgaagcttctgaagagctgatggaaaaatacctgggtggtgaagaactgactgaagcag
aaatcaaaggtgctctgcgtcagcgcgttctgaacaacgaaatcatcctggtaacctgtggttctgcgtt
caagaacaaaggtgttcaggcgatgctggatgcggtaattgattacctgccatccccggttgacgtacct
gcgatcaacggtatcctggacgacggtaaagacactccggctgaacgtcacgcaagtgatgacgagccgt
tctctgcactggcgttcaaaatcgctaccgacccgttgttggtaacctgaccttcttccgtgttactc
                                                    4G3
cggtgtggttaactctggtgataccgtactgaactccgtgaaagctgc[acgtgagcc]tttcggtcgtat
cgttcagatgcacgctaacaaacgtgaagagatcaaagaagttcgcgcgggcgacatcgctgctgctatc
ggtctgaaagacgtaaccactggtgacaccctgtgtgaccggatgcgccgatcattctggaacgtatgg
aattccctgagccggtaatctccatcgcagttgaaccgaaaaccaaagctgaccaggaaaaaatgggtct
ggctctgggccgtctggctaaagaagacccgtctcttccgtgtatggactgacgaagaatctaaccagacc
atcatcgcgggtatgggcgaactgcacctcgacatcatcgttgaccgtatgaagcgtgaattcaacgttg
aagcgaacgtaggtaaaccgcaggttgcttaccgtgaaactatccgccagaaagttaccgatgttgaagg
                            4G6
taaacacgcgaaacagtctggtggtcg[tggtcagta]tggtcatgttgttatcgacatgtacccgctgga
gccggggttcaaacccgaaaggctacgagttcatcaacgacattaaaggtggtgtaatccctggcgaatac
atcccggccgttgataaaggtatccaggaacagctgaaagcaggtccgctggcaggctaccccggtagtag
acatgggtattcgtctgcacttcggttcttaccatgacgttgactcctctgaactggcgttaaactggc
tgcttctatcgccttaaagaaggctttaagaaagcgaaaccagttctgcttgagccgatcatgaacgtt
gaagtagaaactccggaagagaacaccggtgacgttatcggtgacttgagccgtcgtcgtggtatgctca
aaggtcaggaatctgaagttactggcgttaagatccacgctgaagtaccgctgtctgaaatgttcggata
cgcaactcagctgcgttctctgaccaaaggtcgtgcatcatacactatggaattcctgaagtatgatgaa
gcgccgagtaacgttgctcaggccgtaattgaagcccgtggtaaataagcctaaggggttaataccaaagt
cccgtgctctctcctgaaggggagagcactatagtaaggaatatagccgtgtctaaagaaaaatttgaac
gtacaaaaccgcacgttaacgttggtactatcggccacgttgaccacggtaaaactactctgaccgctgc
aatcaccaccgtactggctaaaacctacggcggtgctgctcgtgcattcgaccagatcgataacgcgccg
gaagaaaaagctcgtggtatcaccatcaacacttctcacgttgaatacgacaccccgacccgtcactacg
cacacgtagactgcccggggcacgccgactatgttaaaaacatgatcaccggtgctgctcagatggacgg
cgcgatcctggtagttgctgcgactgacggcccgatgccgcagactcgtgagcacatcctgctgggtcgt
caggtaggcgttccgtacatcatcgtgttcctgaacaaatgcacatggttgatgacgaagagctgctgg
aactggttgaaatggaacttcgtgaacttctgtctcagtacgacttcccgggggcgacgacactccgatcgt
tcgtggttctgctctgaaagcgctggaaggcgacgcagagtgggaagcgaaaatcctggaactggctggc
ttcctggattcttatattccggaaccagagcgtgcgattgacaagccgttcctgctgccgatcgaagacg
tattctccatctccggtcgtggtacc

SEQUENCE LISTING

```
<160> NUMBER OF SEQ ID NOS: 21

<210> SEQ ID NO 1
<211> LENGTH: 1727
<212> TYPE: DNA
<213> ORGANISM: Escherichia coli

<400> SEQUENCE: 1
tttaacccat accagtacaa tggctatggt ttttacattt tacgcaaggg gcaattgtga      60
aactggatga aatcgctcgg ctggcgggag tgtcgcggac cactgcaagc tatgttatta     120
acggcaaagc gaagcaatac cgtgtgagcg acaaaaccgt tgaaaaagtc atggctgtgg     180
tgcgtgagca caattaccac ccgaacgccg tggcagctgg gcttcgtgct ggacgcacac     240
gttctattgg tcttgtgatc cccgatctgg agaacaccag ctatacccgc atcgctaact     300
atcttgaacg ccaggcgcgg caacggggtt atcaactgct gattgcctgc tcagaagatc     360
agccagacaa cgaaatgcgg tgcattgagc acctttttaca gcgtcaggtt gatgccatta     420
ttgtttcgac gtcgttgcct cctgagcatc ctttttatca acgctgggct aacgacccgt     480
tcccgattgt cgcgctggac cgcgccctcg atcgtgaaca cttcaccagc gtggttggtg     540
ccgatcagga tgatgccgaa atgctggcgg aagagttacg taagtttccc gccgagacgg     600
tgctttatct tggtgcgcta ccggagcttt ctgtcagctt cctgcgtgaa caaggtttcc     660
gtactgcctg gaaagatgat ccgcgcgaag tgcatttcct gtatgccaac agctatgagc     720
gggaggcggc tgcccagtta ttcgaaaaat ggctggaaac gcatccgatg ccgcaggcgc     780
tgttcacaac gtcgtttgcg ttgttgcaag gagtgatgga tgtcacgctg cgtcgcgacg     840
gcaaactgcc ttctgacctg gcaattgcca cctttggcga taacgaactg ctcgacttct     900
tacagtgtcc ggtgctggca gtggctcaac gtcaccgcga tgtcgcagag cgtgtgctgg     960
agattgtcct ggcaagcctg gacgaaccgc gtaagccaaa acctggttta acgcgcatta    1020
aacgtaatct ctatcgccgc ggcgtgctca gccgtagcta agccgcgaac aaaaatacgc    1080
gccaggtgaa tttccctctg gcgcgtagag tacgggactg gacatcaata tgcttaaagt    1140
aaataagact attcctgact attattgata aatgcttttta aacccgcccg ttaattaact    1200
caccagctga aattcacaat aattaagtga tatcgacagc gcgttttgc attattttgt     1260 tacatgcggc gatgaattgc cgatttaaca aacacttttc tttgcttttg cgcaaacccg    1320
ctggcatcaa gcgccacaca gacgtaacaa ggactgttaa ccggggaaga tatgtcctaa    1380
aatgccgctc gcgtcgcaaa ctgacacttt atatttgctg tggaaaatag tgagtcattt    1440
taaaacggtg atgacgatga gggattttt cttacagcta ttcataacgt taatttgctt    1500
cgcacgttgg acgtaaaata aacaacgctg atattagccg taaacatcgg gttttttacc    1560
tcggtatgcc ttgtgactgg cttgacaagc ttttcctcag ctccgtaaac tcctttcagt    1620
```

```
gggaaattgt ggggcaaagt gggaataagg ggtgaggctg gcatgttccg gggagcaacg    1680
ttagtcaatc tcgacagcaa agggcgctta tcagtgccta cccgtta                 1727
```

<210> SEQ ID NO 2
<211> LENGTH: 21
<212> TYPE: DNA
<213> ORGANISM: Artificial Sequence
<220> FEATURE:
<223> OTHER INFORMATION: Primer Sequence

<400> SEQUENCE: 2

```
tttaacccat accagtacaa t                                              21
```

<210> SEQ ID NO 3
<211> LENGTH: 21
<212> TYPE: DNA
<213> ORGANISM: Artificial Sequence
<220> FEATURE:
<223> OTHER INFORMATION: Primer Sequence

<400> SEQUENCE: 3

```
taacgggtag gcactgataa g                                              21
```

<210> SEQ ID NO 4
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (13)..(14)
<223> OTHER INFORMATION: "n" represents a, c, g or t

<400> SEQUENCE: 4

```
cgattcgata acnnttcctg                                                20
```

<210> SEQ ID NO 5
<211> LENGTH: 19
<212> TYPE: DNA
<213> ORGANISM: Artificial Sequence
<220> FEATURE:
<223> OTHER INFORMATION: Primer Sequence

<400> SEQUENCE: 5

```
gggcacgatt cgataacta                                                 19
```

<210> SEQ ID NO 6
<211> LENGTH: 19
<212> TYPE: DNA
<213> ORGANISM: Artificial Sequence
<220> FEATURE:
<223> OTHER INFORMATION: Primer Sequence

<400> SEQUENCE: 6

```
gggcacgatt cgataacgc                                                 19
```

<210> SEQ ID NO 7
<211> LENGTH: 3173
<212> TYPE: DNA
<213> ORGANISM: Escherichia coli

<400> SEQUENCE: 7

```
ggtaccagtt gaagtccgtc cggttcgtcg taatgctctg gcaatgcgtt ggatcgttga    60
```

-continued

| | |
|---|---|
| agctgctcgt aaacgcggtg ataaatccat ggctctgcgc ctggcgaacg aactttctga | 120 |
| tgctgcagaa acaaaggta ctgcagttaa gaaacgtgaa gacgttcacc gtatggccga | 180 |
| agccaacaag gcgttcgcac actaccgttg gttatccctt cggagtttta gtcaccaggc | 240 |
| gggcgcttcc agtaagcagc ccgctttggg ctacttaaat tgaacgccta aaagataaac | 300 |
| gaggaaacaa atggctcgta caacacccat cgcacgctac cgtaacatcg gtatcagtgc | 360 |
| gcacatcgac gccggtaaaa ccactactac cgaacgtatt ctgttctaca ccggtgtaaa | 420 |
| ccataaaatc ggtgaagttc atgacggcgc tgcaaccatg gactggatgg agcaggagca | 480 |
| ggaacgtggt attaccatca cttccgctgc gactactgca ttctggtctg gtatggctaa | 540 |
| gcagtatgag ccgcatcgca tcaacatcat cgacaccccg gggcacgttg acttcacaat | 600 |
| cgaagtagaa cgttccatgc gtgttctcga tggtgcggta atggtttact gcgcagttgg | 660 |
| tggtgttcag ccgcagtctg aaaccgtatg gcgtcaggca aacaaatata agttccgcg | 720 |
| cattgcgttc gttaacaaaa tggaccgcat gggtgcgaac ttcctgaaag ttgttaacca | 780 |
| gatcaaaacc cgtctgggcg cgaacccggt tccgctgcag ctggcgattg tgctgaaga | 840 |
| acatttcacc ggtgtgttg acctggtgaa atgaaagct atcaactgga acgacgctga | 900 |
| ccagggcgta accttcgaat cgaagatat cccggcagac atggttgaac tggctaacga | 960 |
| atggcaccag aacctgatcg aatccgcagc tgaagcttct gaagagctga tggaaaaata | 1020 |
| cctgggtggt gaagaactga ctgaagcaga atcaaaggt gctctgcgtc agcgcgttct | 1080 |
| gaacaacgaa atcatcctgg taacctgtgg ttctgcgttc aagaacaaag gtgttcaggc | 1140 |
| gatgctggat gcgtaattg attacctgcc atccccggtt gacgtacctg cgatcaacgg | 1200 |
| tatcctggac gacggtaaag acactccggc tgaacgtcac gcaagtgatg acgagccgtt | 1260 |
| ctctgcactg gcgttcaaaa tcgctaccga cccgtttgtt ggtaacctga ccttcttccg | 1320 |
| tgtttactcc ggtgtggtta actctggtga taccgtactg aactccgtga aagctgcacg | 1380 |
| tgagcgtttc ggtcgtatcg ttcagatgca cgctaacaaa cgtgaagaga tcaaagaagt | 1440 |
| tcgcgcgggc gacatcgctg ctgctatcgg tctgaaagac gtaaccactg gtgacaccct | 1500 |
| gtgtgacccg gatgcgccga tcattctgga acgtatggaa ttccctgagc cggtaatctc | 1560 |
| catcgcagtt gaaccgaaaa ccaaagctga ccaggaaaaa atgggtctgg ctctgggccg | 1620 |
| tctggctaaa gaagacccgt ctttccgtgt atggactgac gaagaatcta accagaccat | 1680 |
| catcgcgggt atgggcgaac tgcacctcga catcatcgtt gaccgtatga gcgtgaattt | 1740 |
| caacgttgaa gcgaacgtag gtaaaccgca ggttgcttac cgtgaaacta tccgccagaa | 1800 |
| agttaccgat gttgaaggta acacgcgaa acagtctggt ggtcgtggtc agtatggtca | 1860 |
| tgttgttatc gacatgtacc cgctggagcc gggttcaaac ccgaaaggct acgagttcat | 1920 |
| caacgacatt aaaggtggtg taatccctgg cgaatacatc ccggcgttg ataaaggtat | 1980 |
| ccaggaacag ctgaaagcag gtccgctggc aggctacccg gtagtagaca tgggtattcg | 2040 |
| tctgcacttc ggttcttacc atgacgttga ctcctctgaa ctggcgtttaa actggctgc | 2100 |
| ttctatcgcc tttaaagaag gctttaagaa agcgaaacca gttctgcttg agccgatcat | 2160 |
| gaaggttgaa gtagaaactc cggaagagaa caccggtgac gttatcggtg acttgagccg | 2220 |
| tcgtcgtggt atgctcaaag gtcaggaatc tgaagttact ggcgttaaga tccacgctga | 2280 |
| agtaccgctg tctgaaatgt tcggatacgc aactcagctg cgttctctga ccaaaggtcg | 2340 |
| tgcatcatac actatggaat tcctgaagta tgatgaagcg ccgagtaacg ttgctcaggc | 2400 |
| cgtaattgaa gcccgtggta ataagcctaa agggttaata ccaaagtccc gtgctctctc | 2460 |

```
ctgaagggga gagcactata gtaaggaata tagccgtgtc taaagaaaaa tttgaacgta    2520
caaaaccgca cgttaacgtt ggtactatcg gccacgttga ccacggtaaa actactctga    2580
ccgctgcaat caccaccgta ctggctaaaa cctacggcgg tgctgctcgt gcattcgacc    2640
agatcgataa cgcgccggaa gaaaaagctc gtggtatcac catcaacact tctcacgttg    2700
aatacgacac cccgacccgt cactacgcac acgtagactg cccggggcac gccgactatg    2760
ttaaaaacat gatcaccggt gctgctcaga tggacggcgc gatcctggta gttgctgcga    2820
ctgacggccc gatgccgcag actcgtgagc acatcctgct gggtcgtcag gtaggcgttc    2880
cgtacatcat cgtgttcctg aacaaatgcg acatggttga tgacgaagag ctgctggaac    2940
tggttgaaat ggaagttcgt gaacttctgt ctcagtacga cttcccgggc gacgacactc    3000
cgatcgttcg tggttctgct ctgaaagcgc tggaaggcga cgcagagtgg gaagcgaaaa    3060
tcctggaact ggctggcttc ctggattctt atattccgga accagagcgt gcgattgaca    3120
agccgttcct gctgccgatc gaagacgtat tctccatctc cggtcgtggt acc           3173
```

<210> SEQ ID NO 8
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (12)..(14)
<223> OTHER INFORMATION: "n" represents a, c, g or t

<400> SEQUENCE: 8
gattcgataa cnnnctgcaa                                                  20

<210> SEQ ID NO 9
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (12)..(14)
<223> OTHER INFORMATION: "n" represents a, c, g or t

<400> SEQUENCE: 9
gattcgataa cnnntgagcg                                                  20

<210> SEQ ID NO 10
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (12)..(14)
<223> OTHER INFORMATION: "n" represents a, c, g or t

<400> SEQUENCE: 10
gattcgataa cnnntgacca                                                  20

<210> SEQ ID NO 11
<211> LENGTH: 20
<212> TYPE: DNA
<213> ORGANISM: Artificial Sequence
<220> FEATURE:

```
<223> OTHER INFORMATION: Primer Sequence

<400> SEQUENCE: 11
gggcacgatt cgataactac                                              20

<210> SEQ ID NO 12
<211> LENGTH: 19
<212> TYPE: DNA
<213> ORGANISM: Artificial Sequence
<220> FEATURE:
<223> OTHER INFORMATION: Primer Sequence

<400> SEQUENCE: 12
ggcacgattc gataacacg                                               19

<210> SEQ ID NO 13
<211> LENGTH: 19
<212> TYPE: DNA
<213> ORGANISM: Artificial Sequence
<220> FEATURE:
<223> OTHER INFORMATION: Primer Sequence

<400> SEQUENCE: 13
ggcacgattc gataacgcg                                               19

<210> SEQ ID NO 14
<211> LENGTH: 30
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (22)..(24)
<223> OTHER INFORMATION: "n" represents a, c, g or t

<400> SEQUENCE: 14
cacacaggaa acagctatga cnnncgctac                                   30

<210> SEQ ID NO 15
<211> LENGTH: 30
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (22)..(24)
<223> OTHER INFORMATION: "n" represents a, c, g or t

<400> SEQUENCE: 15
cacacaggaa acagctatga cnnncgattt                                   30

<210> SEQ ID NO 16
<211> LENGTH: 30
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (22)..(24)
<223> OTHER INFORMATION: "n" represents a, c, g or t

<400> SEQUENCE: 16
cacacaggaa acagctatga cnnnaacgca                                   30
```

```
<210> SEQ ID NO 17
<211> LENGTH: 24
<212> TYPE: DNA
<213> ORGANISM: Artificial Sequence
<220> FEATURE:
<223> OTHER INFORMATION: Primer Sequence

<400> SEQUENCE: 17
cacacaggaa acagctatga cctt                                              24

<210> SEQ ID NO 18
<211> LENGTH: 24
<212> TYPE: DNA
<213> ORGANISM: Artificial Sequence
<220> FEATURE:
<223> OTHER INFORMATION: Primer Sequence

<400> SEQUENCE: 18
cacacaggaa acagctatga cggt                                              24

<210> SEQ ID NO 19
<211> LENGTH: 24
<212> TYPE: DNA
<213> ORGANISM: Artificial Sequence
<220> FEATURE:
<223> OTHER INFORMATION: Primer Sequence

<400> SEQUENCE: 19
cacacaggaa acagctatga cggt                                              24

<210> SEQ ID NO 20
<211> LENGTH: 23
<212> TYPE: DNA
<213> ORGANISM: Artificial Sequence
<220> FEATURE:
<223> OTHER INFORMATION: Primer Sequence

<400> SEQUENCE: 20
gtcgataaat gggcaatacg aac                                               23

<210> SEQ ID NO 21
<211> LENGTH: 17
<212> TYPE: DNA
<213> ORGANISM: Artificial Sequence
<220> FEATURE:
<223> OTHER INFORMATION: Primer Sequence

<400> SEQUENCE: 21
caggaaacag ctatgac                                                      17
```

METHOD OF AMPLIFICATION OF NUCLEIC ACIDS

TECHNICAL FIELD

The present invention relates generally to genetic analysis and, in particular, to genomics. More specifically, the invention relates to a method of amplification of a nucleic acid (or a nucleotide sequence of interest) which may be applied to sequencing in general and, in particular, to genome sequencing.

BACKGROUND ART

The development of methods for automated DNA sequence analysis, together with advances in bioinformatics, has revolutionised biology and medicine and ushered in the new field of genomics—the study of genes and genomes. These techniques have been used to decipher the entire genomes of a number of bacteria (5, 7, 9, 10, 20), archea (3) and eukaryotes (6, 11).

The traditional approach to sequencing large genomes, including the human genome, uses a three-stage divide-and-conquer strategy (29). The first stage involves the construction of a number of clone libraries of the study organism's DNA by randomly cutting the DNA into fragments, separating these into differing size classes, and then inserting the fragments into appropriate vectors capable of propagation in a yeast or bacterial host.

The second stage involves (a) construction of a low-resolution physical map by identification of shared chromosomal landmarks on overlapping yeast or bacterial artificial chromosome (YAC or BAC) clones. The landmarks may be, for example, unique sites that can be amplified by polymerase chain reaction (PCR) (sequence-tagged sites or STSs) or restriction-enzyme digestion sites; (b) the construction of high-resolution (sequence ready) maps by randomly subcloning YAC or BAC inserts into cosmid vectors and identifying their landmark overlaps.

The third and final stage involves selecting a minimally overlapping set of cosmid clones, randomly fragmenting each into small pieces, and subcloning into M13 phage or plasmid vectors. For each cosmid approximately 800 M13 phase clones are sequenced and assembled to construct the sequence of the 40-kilobase (Kbp) cosmid insert. This random (shogun) approach is redundant as ever nucleotide is sequenced about eight times.

The complexity and cost of the "divide-and-conquer" approach has driven the development of new strategies. The Institute for Genomic Research (TIGR) has pioneered the direct shogun sequencing of megabase-sized (Mbp) genomes. In this approach, the small fragments of chromosomal DNA are cloned directly into the M13 vector. Clones are randomly sequenced and the chromosome sequence constructed by direct assembly. This whole-genome random sequencing strategy has been applied to the sequencing of a number of bacterial and archeal genomes, including the 1.9 Mbp genome of *Haemophilus influenzae* (9), the 0.58 Mbp genome of *Mycoplasma genitalium* (10), and the 1.66 Mbp genome of *Methanococcus jannaschii* (3). This approach eliminates the need for any prior physical mapping, significantly reducing the overall per base pair cost of producing a finished sequence. However, as with all random sequencing approaches, the inherent problem is the requirement for a high level of sequence redundancy. In other words, every nucleotide has to be sequenced numerous times until, by computer alignment, sequence contigs (clusters of aligned sequences) can be constructed. The initial shotgun assembly of the *H. influenzas* genome, for example, involved the generation of 11.6 Mbp of random sequence data (greater than 6-fold genome coverage), and yet still contained 140 contig gaps requiring labour intensive closure (9).

An alternative to the inherent inefficiencies of random shogun sequencing is primer walking (25). In this procedure, a primer designed from a known sequence is used to extend sequence information into the flanking unknown region. The new sequence information is used to design the next primer, and the process is continued until the entire sequence of the region of interest is determined. Although the primer walking strategy appears attractive for large-scale sequencing projects, the need for time-consuming and expensive synthesis of individual primers every 400 to 500 bp makes it impracticable. The use of a presynthesized library of short primers would avoid the requirement for the synthesis of each new primer. Unfortunately, libraries of even relatively short primers are enormous, for example, a complete octamer library contains 65.536 primers, while a complete decamer library contains over a million individual primers.

Two basic solutions have been proposed to enable primer walking and yet avoid the synthesis of large primer libraries. The first involves reducing the size of the primer libraries by selecting an optimise subsets of useful octamers, nonamers, or decamers (4, 12, 24, 26). The second, Sequential Primer Elongation by Ligation of 6-mers (SPEL-6), involves the assembly of large primers (18 bp or longer) by the annealing of at least three contiguous complementary hexamers (drawn from a presynthesized library of the full set of all 4096 hexamers or 1024 singly degenerated hexamers) to a single stranded DNA template. The annealed hexamers are joined by libation and a standard sequencing reaction performed (15–19, 27). A number of related techniques based on this approach have been developed, including the use of hexamers but omitting ligation (21, 22), or based on the ligation of self-complementary hexamer strings (8).

A large number of technical difficulties exist with both approaches which has prevented their wide-spread use. Simulation studies of large sequencing projects have suggested that reduction of primer sets by more than 80% to 90% affects priming flexibility and general utility (1, 26). In the case of an octamer primer library, this results in library sets containing 6,000 to 12,000 primers, with a nonamer primer library requiring four times as many primers. While primer libraries of this size are technically possible, they would be both expensive to construct and unwieldy to use. A number of investigators have designed smaller octamer and nonamer primer sets containing 1000 to 3000 primers, however, these sets are limited in use to protein coding sequences with little G-C variability (12, 14, 24). Of a more fundamental nature is the failure of many short oligonucleotides to successfully prime sequencing reactions, for example, in one report only approximately one half of 121 nonamer primers worked (2). This common problem appears linked to the formation of template secondary structures which prevent efficient binding of the primer to the correct site (18).

The complexity of the SPEL-6 hexamer libation strategy has limited its utility for large-scale sequencing projects. In addition to a complete hexamer primer library (containing 4096 primers), this technique requires: (1) enzymatic phosphorylation of the hexamer primers, (2) a single-stranded DNA template or chemical denaturation of double stranded DNA, (3) a DNA ligation reaction in the presence of single stranded binding protein, (4) a deproteination step before sequencing, and (5) the use of the Sequence enzyme (18). In addition, sequencing failures are common, as the low annealing temperature required for hexamer primer annealing also promotes the formation of template secondary hairpin structures that prevent efficient primer annealing. Finally, both the reduced library and the SPEL-6 approaches are unable to use fluorescent-labelled primers, and are thus limited in the use of sequencing hardware and chemistries.

It is an object of the present invention to overcome or ameliorate at least one of the disadvantages of the prior art, or to provide a useful alternative.

SUMMARY OF THE INVENTION

The present invention relates to a method of amplification of a nucleotide sequence utilising interlaced nesting primers. The method may be used for sequencing purposes and, in particular, for genome sequencing. The method when applied to sequencing has been coined Amplification and Sequencing by Interlaced Nesting (ASIN).

According to a first aspect, the present invention provides a method of amplifying a nucleotide sequence of interest wherein the nucleotide sequence comprises at least one region of known sequence, wherein the region of known sequence comprises, 3' to 5': a first known region and a second known region wherein the first and second known regions are immediately adjacent each other and wherein the method comprises:

1) a first amplification step comprising at least
   (a) as a template, a sequence comprising at least the nucleotide sequence of interest; and
   (b) one first primer having, 5' to 3': a 5' tag sequence; a degenerate sequence corresponding to the first known region; and a sequence complementary to the second known region of the nucleotide of interest;
which amplification step generates a first amplification product; and
2) a second amplification step comprising at least
   (a) as a template, the first amplification product; and
   (b) one second primer having, 5' to 3': a sequence which hybridises to the complementary strand of the 5' tag sequence of the first primer and a sequence complementary to the first known region of the nucleotide sequence of interest; which amplification step generates a second amplification product.

Preferably, the amplification step is a polymerase chain reaction (PCR).

Preferably, in the first and second primers respectively, the 5' tag sequence and the sequence which hybridises to the complementary strand of the 5' tag sequence of the first primer, are the same.

Preferably, the 5' tag sequence is a vector specific sequence. More preferably, the 5' tag sequence is derived from M13 phage, pUC18, pBR322, pGEM®, BLUESCRIPT, or pBELOBACII. However, the skilled addressee will, of course, understand that any appropriate 5' tag sequence can be used.

Preferably, the 5' tag sequence is 10 to 25 bases in length. More preferably, the 5' tag sequence is 15 to 18 bases in length. Most preferably, the 5' tag sequence is 15 bases in length.

Preferably, in the first primer, the sequence complementary to the second known region is 4 to 8 bases in length. More preferably, in the first primer, the sequence complementary to the second known region is 6 bases in length.

Preferably, in the first primer, the degenerate sequence together with the sequence complementary to the second known region of the nucleotide of interest is 6 to 12 bases in length. Most preferably, in the first primer, the degenerate sequence together with the sequence complementary to the second known region of the nucleotide of interest is 9 bases in length.

Preferably, in the second primer, the sequence complementary to the first known region of the nucleotide sequence of interest is 1 to 5 bases in length. More preferably, in the second primer, the sequence complementary to the first known region of the nucleotide sequence of interest is 3 bases in length.

Preferably, the 5' tag sequence, or a sequence which hybridises to the complementary sequence of the 5' tag sequence, is used as a sequencing primer. Alternatively, the second primer is used as a sequencing primer.

In one embodiment, the first and second amplifications comprise two first primers and two second primers respectively, wherein one of the first primers acts as a reverse primer in the first amplification step and one of the second primers acts as a reverse primer in the second amplification step. It will be clear to the skilled addressee that the 5' tag sequence on each of the first primers may be the same or different.

It will also be clear to the skilled addressee that steps 1) and 2) may be performed sequentially or simultaneously.

According to a third aspect, the present invention provides a product when obtained by a method according to the first or second aspect.

According to a fourth aspect, the present invention provides a primer having, 5' to 3': a 5' tag sequence: a degenerate sequence: and a predetermined sequence, wherein the sequences are immediately adjacent to each other. Preferably, the predetermined sequence is 4 to 8 bases in length and more preferably it is 6 bases in length. Preferably, the degenerate sequence together with the predetermined sequence is 6 to 12 bases in length and more preferably, it is 9 bases in length.

According to a fifth aspect, the present invention provides a primer having, 5' to 3': a sequence which hybridises to the complementary strand of the 5' tag sequence of a primer according to the fourth aspect, and a predetermined sequence. Preferably, the predetermined sequence is 1 to 5 bases in length and more preferably it is 3 bases in length.

The 5' tag sequence of the primers of the fourth and fifth aspects may be a vector specific sequence such as that derived from M13 phage, pUC18, pBR322, pGEM, BLUESCRIPT, or pBELOBACII. Preferably the primers of the fourth and fifth aspects are 10 to 25 bases in length, more preferably 15 to 18 bases in length and most preferably 15 bases in length.

According to a sixth aspect, the present invention provides a primer set comprising at least two primers wherein the primers are selected from primers according to the fourth or fifth aspect. The primer set may be a primer set in which at least one primer is a primer according to the fourth aspect and at least one primer is a primer according to the fifth aspect.

According to a seventh aspect, the present invention provides a primer library comprising primers according to the fourth aspect.

According to an eighth aspect, the present invention provides a primer library comprising primers according to the fifth aspect.

According to a ninth aspect, the present invention provides a primer library comprising primers according to the fourth or fifth aspect.

According to a tenth aspect, the present invention provides a primer library comprising primer sets according to the sixth aspect.

The libraries may be produced by any means known to persons skilled in the art. Preferably, the libraries are produced by chemical synthesis using the phosphoramidite method.

According to an eleventh aspect, the present invention provides a kit comprising a primer according to the fourth or fifth aspect.

According to a twelfth aspect, the present invention provides a kit comprising a primer set according to the sixth aspect.

According to a thirteenth aspect, the present invention provides a kit comprising a primer library according to any one of the seventh to tenth aspects.

Preferably, the kit is used in the method of the first or second aspect. It will be appreciated that the kit may further include optional buffers, diluents, enzymes, and a sample of one or more suitable reverse primers.

According to a fourteenth aspect, the present invention provides a method of amplifying and sequencing a nucleotide sequence of interest wherein the nucleotide sequence comprises at least one region of known sequence, wherein the region of known sequence comprises, 3' to 5': a first known region of 3 bases and a second known region of 6 bases wherein the first and second known regions are immediately adjacent each other and wherein the method comprises:

1) a first amplification step comprising at least
   (a) as a template, a sequence comprising at least the nucleotide sequence of interest; and
   (b) one first primer having, 5' to 3': a 5' tag sequence; a degenerate sequence corresponding to the first known region; and a sequence complementary to the second known region of the nucleotide of interest;
which amplification step generates a first amplification product; and
2) a second amplification step comprising at least
   (a) as a template, the first amplification product; and
   (b) one second primer having, 5' to 3': the same 5' tag sequence as the first primer and a sequence complementary to the first known region of the nucleotide sequence of interest
which amplification step generates a second amplification product;
3) sequencing the second amplification product using the 5' tag sequence as a sequencing primer.

According to a fifteenth aspect, the present invention provides a method of amplifying and sequencing a nucleotide sequence of interest wherein the nucleotide sequence comprises at least one region of known sequence, wherein the region of known sequence comprises, 3' to 5': a first known region and a second known region wherein the first and second known regions are immediately adjacent each other and wherein the method comprises:

1) an amplification step comprising at least
   (a) as a template, a sequence comprising at least the nucleotide sequence of interest; and
   (b) one primer having, 5' to 3': a 5' tag sequence; a degenerate sequence corresponding to the first known region; and a sequence complementary to the second known region of the nucleotide of interest;
which amplification step generates an amplification product; and
2) a sequencing step in which the amplification product is sequenced using a sequencing primer.

Preferably, the sequencing step of the fifteenth aspect comprises at least (a) as a template, the amplification product; and
   (b) the sequencing primer having, 5' to 3': a sequence which hybridises to the complementary strand of the 5' tag sequence of the primer utilised in the amplification step, and a sequence complementary to the first known region of the nucleotide of interest.

According to a sixteenth aspect, the present invention provides a method of amplifying and sequencing a nucleotide sequence of interest wherein the nucleotide sequence comprises at least one region of known sequence, wherein the region of known sequence comprises, 5' to 3': a first known region and a second known region wherein the first and second known regions are immediately adjacent each other and wherein the method comprises:

1) an amplification step comprising at least
   (a) as a template, a sequence comprising at least the nucleotide sequence of interest; and
   (b) one primer having, 5' to 3': a 5' tag sequence: a degenerate sequence corresponding to the first known region: and a sequence complementary to the second known region of the nucleotide of interest;
which amplification step generates an amplification product;
2) a sequencing step in which the amplification product is sequenced using a sequencing primer.

Preferably, the sequencing step of the sixteenth aspect comprises at least (a) as a template, the amplification product; and
   (b) the sequencing primer having, 5' to 3': a sequence which hybridises to the complementary strand of the 5' tag sequence of the primer utilised in the amplification step, and a sequence complementary to the first known region of the nucleotide of interest.

Preferably, the amplification step of the sixteenth aspect is a polymerase chain reaction. In the primer utilised in the amplification step and in the sequencing primers respectively, the 5' tag sequence and the sequence which hybridises to the complementary strand of the 5' tag sequence of the primer utilised in the amplification step, may be the same or different. The 5' tag, sequence may be a vector specific sequence such as M13 phage, pUC18, pBR322, pGEM, BLUESCRIPT, or pBELOBACII. Preferably, the 5' tag sequence is 10 to 25 bases in length, more preferably 15 to 18 bases in length and most preferably 15 bases in length. In the method of the sixteenth aspect, in the primer utilised in the amplification step, the sequence complementary to the second known region may be 4 to 8 bases in length and more preferably, 6 bases in length. In the primer utilised in the amplification step, the degenerate sequence together with the sequence complementary to the second known region of the nucleotide of interest is 6 to 12 bases in length, more preferably 9 bases in length. In the sequencing primer, the sequence complementary to the first known region of the nucleotide sequence of interest may be 1 to 5 bases in length, more preferably 3 bases in length.

It will be clear to the skilled addressee that, since the primers of the invention can be used as forward and reverse primers, the methods described above can be used to amplify (and sequence) any desired nucleotide sequence. It is also clear that since large parts of the genome sequence of some organisms, and the entire genome sequence of others is known, the invention could be used to generate a library or an array of sequences of, say, open reading frames of an organism.

According to a seventeenth aspect, the present invention provides a product produced by a method according to any one the fourteenth to the seventeenth aspects.

According to an eighteenth aspect, the present invention provides a kit comprising a product of the third or eighteenth aspects.

According to a nineteenth aspect, the present invention provides a method according to any one the first or second aspects or the fourteenth to seventeenth aspects when used in a method of primer walking.

According to a twentieth aspect, the present invention provides a product according to the third aspect, when used in a method of primer walking.

According to a twenty-first aspect, the present invention provides a primer according to the fourth or fifth aspect, when used in a method of primer walking.

According to a twenty-second aspect, the present invention provides a primer set according to the sixth aspect, when used in a method of primer walking.

According to a twenty-third aspect, the present invention provides a primer library according to any one of the seventh to tenth aspects, when used in a method of primer walking.

According to a twenty-fourth aspect, the present invention provides a kit according to any one of the eleventh to thirteenth aspects, when used in a method of primer walking.

General laboratory procedures not specifically described in this specification can be found in the general molecular biology texts including, for example, Sambrook et al. (1989) Molecular Cloning: A laboratory Manual. Cold Spring Harbor Laboratory:Cold Spring Harbor, N.Y.

In the context of the present specification the terms "polymerase chain reaction" and its acronym "PCR" are used according to their ordinary meaning as understood by those skilled in the art. Examples of PCR methods can be found in common molecular biology textbooks and reference manuals used in the art. For example PCR Technology: Principles and Applications for DNA Amplification (1989) Ed. H. A. Erlich Stockton Press, New York.

In order to optimise the PCR amplification, the primers can be used at different concentrations and ratios. Selection of these and other variables would be appreciated and obtainable by persons skilled in the art.

In the context of the present invention, the terms "to amplify" and "amplification" should be construed in the sense of "to produce at least one copy of" and "the production of at least one copy of".

In the context of the present invention, the term "sequencing primer" should be construed in the sense of any primer which can initiate a sequencing reaction.

In the context of the present invention, the terms "oligonucleotide", "nucleic acid", "nucleotide sequence" and "template" should be construed according to their ordinary meaning as understood by the skilled addressee.

In the context of the present specification, the term "primer walking" should be construed according to its ordinary meaning as understood by those skilled in the art, i.e. in the sense of utilising a known nucleotide sequence to obtain nucleotide sequence from an unknown flanking region and utilising the nucleotide sequence thus obtained to obtain further nucleotide sequence from a further flanking region. The process can be repeated any number of times.

Unless the context clearly requires otherwise, throughout the description and the claims, the words "comprise", "comprising", and the like are to be construed in an inclusive sense as opposed to an exclusive or exhaustive sense: that is to say, in the sense of "including, but not limited to".

BRIEF DESCRIPTION OF THE DRAWINGS

FIG. 1 is a schematic outline of an ASIN procedure according to the present invention. The spotted region represents the 5' tag sequence, the striped region represents the first known region, and the grey region represents the second known region.

FIG. 3. The 1727 bp E. coli fruR region PCR amplified with the primers EK10R and EK10FS. The annealing sites of EK10R and EK10FS are underlined. The three 8 nucleotide long annealing sites of the first round ASIN primer TTCCTG are boxed. PCR amplification using the ASIN second round primer CTAG-GC and CTAG-TA will result in a PCR products of 1108 bp and 595 bp, respectively.

FIG. 5. The 3172 bp E. coli fusA region. The three 9 nucleotide long annealing sites of the first round ASIN primers 4G1, 4G3 and 4G6 are boxed. PCR amplification using the ASIN second round primer 4G9 and 4G12 or 4G7 and 4G12 will result in PCR products of 509 bp and 1440 bp, respectively.

DESCRIPTION OF THE INVENTION

Figure 2:
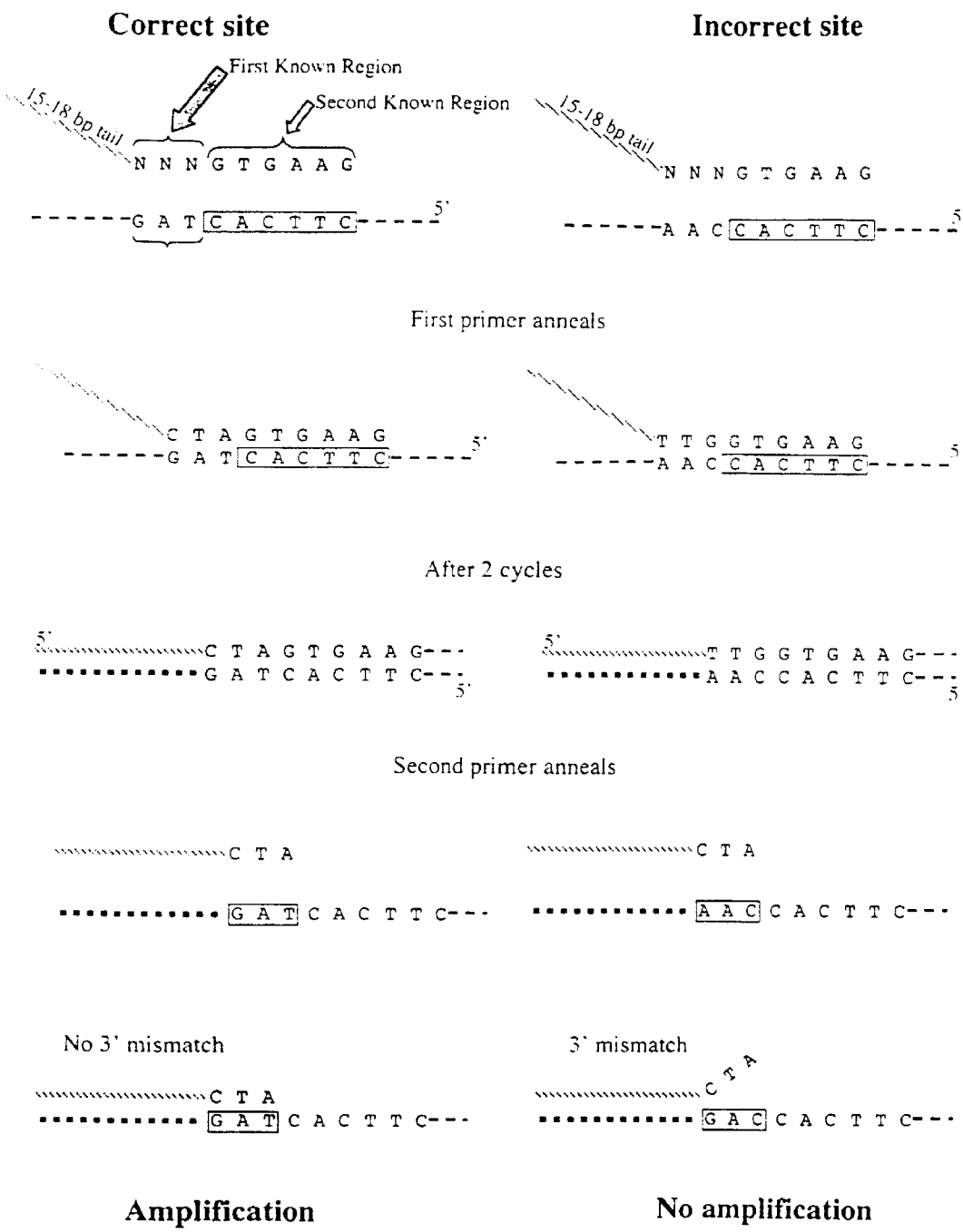
FIG. 2 shows a diagrammatic example of the suppression of non-desired PCR products by a nesting reaction of the ASIN procedure according to the present invention. The first and second known regions of the nucleotide sequence of interest are indicated.

The present invention relates to a method of amplifying a nucleotide sequence of interest when a region of the nucleotide sequence is known. The method may be utilised in sequencing protocols, particularly in genome sequencing, and may provide advantages over current sequencing techniques.

The present invention may be used for primer walking on an amplifiable template using primers selected from a relatively small presynthesized library. This approach can be used with many different sequencing chemistries and is suitable for automation.

In order that the present invention may be more clearly understood, preferred forms will be described in the following examples with reference to the accompanying drawings.

Although the observation appears to have been little appreciated, it has been shown that successful PCR can be performed with primers that only anneal to the template over the final 8 to 11 bp (23). In other words, provided an oligonucleotide matches the template for 8 or more bases at its 3' end, it can act as a PCR primer.

A complete octamer primer library which could be used to amplify any template (of which at least eight bases were known) would contain 65.536 primers, while a complete nonamer primer library would contain 262.144 primers. Even a 90% reduction of such a library set would still leave this library cumbersome. The present invention allows the number of primers in a complete library i.e. a library which may be used to amplify any template (of which at least some sequence is known) to be greatly reduced by careful primer design.

In accordance with this invention, using a two-step amplification procedure, the specificity of, for example, a nondegenerate nonamer primer library can be obtained from a much smaller degenerate nonamer primer library described below. A schematic diagram of an example of the two-step procedure is illustrated in FIG. 1 and describes the amplification of a template nucleotide sequence of interest of which 9 bases (divided into a "first known region" and a "second known region") are known.

The invention requires the addition of a 5' tag sequence to the nonamer primer. As shown in the example, each primer in the nonamer primer library is made partially degenerate (by introducing all four bases at, for example, positions 7, 8, and 9 (from the 3' end)), the required library can be reduced 64-fold. Thus, the "nonamer" primer library can be constructed from only 4096 primers, each primer including 3 degenerate positions 7 to 9 bases from its 3' end. Although this reduces the number of primers required, it also effectively transforms the nonamer primer library into a hexamer primer library of 4096 members, and hence greatly reduces the amplification specificity. Primers from this library may be prone to mispriming as annealing sites would exist, on average, every 4 Kb of template, as compared to every 262 Kb for a true nonamer primer.

A 5' tagged degenerate nonamer primer is selected from the library, such that it will anneal to 6 bases (the "second known region") at the 3' end of the 9 known bases of template. As the degenerate nonamer primer is actually a mixture of 64 related primers, amplification using this degenerate primer will potentially result in a mixture of different products, of which the desired product may be a minor component.

The desired product can then be selectively amplified from this mix by the use of a second primer. This second primer is selected from a second primer library which may include (as shown for example in FIG. 2) 64-members, in which each primer contains the same 5' tag sequence as the primers in the first library (or a sequence which will hybridise to the complementary strand of the 5' tag sequence of the primers in the first library), and one of the 64 possible combinations of 3 nucleotides at its 3' end. The second primer is selected from this 64-member library on the basis of the complementarity of its combination of 3 nucleotides (at the 3' end) to the 3 bases residing 5' to the 6 bases of template utilised to select the first primer (the "first known region") (FIG. 2). Since non-desired products will contain 3' primer-template mismatches in the 3 nucleotides (as shown in FIG. 2), the desired product will be selectively amplified from the product mix.

A reverse primer is, of course, required. However, if the template to be sequenced is from a cloned library, for example, a common vector-specific reverse primer can be used. The resultant PCR product will contain, 5' to 3', the 5' tag sequence: the "known" 9 bp sequence: and the flanking unknown sequence.

Thus, as indicated above, the specificity of, for example, a true nonamer primer library can be obtained using a combination of a vastly smaller degenerate (hexamer) first primer library and a second, 64-member primer library.

The product of the two PCRs can, of course, be sequenced by any known sequence chemistry. Primer walking can be performed using a 5' tagged octamer or nonamer primer library by selecting the appropriate primer (ie. the primer which has a 3' match with the template at the desired location) and performing a PCR. The sequence of the region flanking the "known" sequence described above, can then be obtained using either (a) the 5' tag alone, or (b) the second primer, as a primer. This process can be repeated by using the sequence information to select a new primer from the 5' tagged primer library, until the entire sequence of the nucleotide sequence of interest is determined.

A number of adaptations/modifications of the procedure outlined above are contemplated. For example, first, the procedure can be performed as either two separate amplification reactions, or as a one-step procedure by including all three primers in one reaction but reducing the concentration of the first (degenerate) primer 10 to 100-fold. In this way, amplification specificity is maintained as the early exhaustion of the first 5' tagged primer ensures that amplification in the later stages is predominantly due to the second 5' tagged primer.

Further, it is possible to perform the amplification with two sets of first and second primers i.e. without a conventional reverse primer. It may therefore, be possible to use this approach as a means to perform general amplification reactions by selecting two sets of primers, thus avoiding the need to synthesise primers specifically for each template (provided, of course, the required minimum number of bases were known at each end of the desired product).

The first (degenerate) primer library has been exemplified as a 5' tagged nonamer primer library but, of course, need not necessarily be based on nonamers and may be, for example, octamers or decamers or any other useful length of primer. The length of the primer required can be established by simple experimentation by the skilled addressee. Equally, the second primer library does not have to be based on trimers, as exemplified above, but could instead, for example, be based on doublets or fourmers or any other useful length of primer. Again, the length of the primer required can be easily ascertained by the skilled addressee by simple experimentation. Further, the size of the first (degenerate) primer library can he reduced. For example, a degenerate nonamer primer library could be reduced from 4096 primers to approximately 400 primers by omission of 90% of the 4096 primers.

Any template which is amplifiable can be used in this invention including genomic DNA, plasmid clones, cDNA, etc.

It would also be possible, although more cumbersome, to amplify and sequence a nucleotide sequence of interest, using a library of primers which simply contain a common 5' tag sequence (eg. the M13 reverse primer) and, for example, all possible 8 or 9 bp 3' ends to amplify any desired nucleotide sequence of interest of which, for example, at least 8 or 9 bp are known, respectively. In this method, a second primer as described above is not required. Again, when the nucleotide sequence of interest is included in a vector, a reverse primer may be designed based on the vector sequence at the 3' end of the nucleotide sequence of interest.

This amplification-based primer walking approach may have a number of advantages over other primer-library, or hexamer-ligation based, approaches. First, this approach can avoid problems associated with template secondary structure formation as the walking amplification can be performed at a high annealing temperature after the first cycle, that is, once the 5' tagged primer has annealed to the template for the first time, the annealing site becomes, on the subsequent cycles, both the 5' tag sequence plus the original 8 or 9 bp site. In other words, the 5' tagged primer only has to "catch" once to enable the amplification reaction to proceed. Thus, if the original 5' tagged primer anneals poorly, because of secondary structure constraints, the primer 5' tag sequence ensures efficient amplification. Secondly, standard sequencing conditions can be used as the same common 5' tag sequence is introduced into each amplification product. Thirdly, labelled sequencing primers may be used, thus making this approach compatible with all sequencing chemistries (eg. Licor). Fourthly, complex enzymatic steps required for other sequencing technologies, such as SPEL-6 hexamer libation approach, can be avoided.

The skilled addressee will recognise that greater sequence specificity can be obtained by performing extra nested amplification reactions. For example, 12-mer specificity could be obtained by designing three primer libraries and performing two nested amplification reactions.

EXAMPLE 1

PCR amplification of the fruR gene of E. coli

A 1727 bp fragment of the E. coli genome containing the fruR gene (SEQ ID No. 1) was PCR amplified (FIG. 3). The PCR reaction contained: 5 μl of a 2 mM deoxynucleotide triphosphate mix (dNTP) of all four deoxynucleotide triphosphates: 5 μl of 10×PCR buffer [500 mM KCl, 100 mM Tris-HCl (pH 9.0 at 25° C.). 1% TritonX-100]; 4 μl of 25 mM MgCl$_2$; 1 μl of the EK10FS primer (5'-tttaacccataccagtacaat-3': SEQ ID No. 2) (10 pmol per μl); 1 μl of the EK10R primer (5'-taacgggtaggcactgataag-3': SEQ ID No. 3) (10 pmol per μl); 1 μl of E. coli DNA (10 ng per μl); and 28 μl of milliQ water. The PCR reaction was preheated to 80° C. in a PE 2400 PCR machine and 5 μl of MilliQ water added containing 1 unit of Taq DNA polymerase and 0.1 unit of Pfu DNA polymerase. The reaction was subjected to 10 cycles of: 95° C. for 10 s, 65° C. for 20 s reducing by 1° C. per cycle, and 72° C. for 90 s. The PCR reaction was immediately subjected to a further 20 cycles of: 95° C. for 10 s, 54° C. for 20 s. 72° C. for 90 s.

ASIN PCR #1

Nested PCR amplifications of the 1727 bp E. coli fruR region were performed using the ASIN procedure. First round ASIN PCR amplifications contained: 1 μl of 2 mM dNTPs: 1 μl of 10×PCR buffer: 1 μl of 25 mM MgCl$_2$: 1 μl of the first round ASIN primer TTCCTG (5'-cgattcgataacnnnttcctg-3': SEQ ID No. 4) (1 pmol per μl); 0.2 μl of the fruR PCR product as template DNA: 1 unit of Taq DNA polymerase: and 5.6 μl of MilliQ water. PCR reactions were preheated to 95° C. for 30 s before 2 cycles of: 95° C. for 10 s. 40° C. for 60 s. 72° C. for 60 s.

ASIN PCR #2

Figure 4:
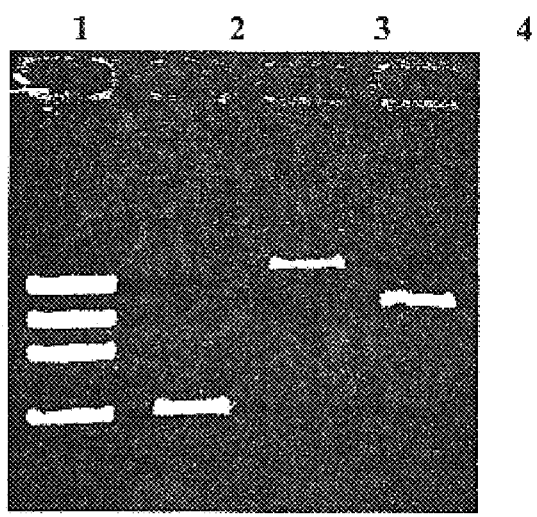
FIG. 4. ASIN PCR reactions using the first round primer TTCCTG and the second round primers CTAG-GC and CTAG-TA. Lane 1: 150 ng of f174 DNA marker (1353, 1078, 872 and 603 bp). Lane 2: 6 μl of the ASIN PCR amplification using the second round primers CTAG-TA and EK10R. Lane 3: 1 μl of the fruR PCR product. Lane 4: 6 μl of the ASIN PCR amplification using the second round primers CTAG-GC.

The second round ASIN PCR mixes contained: 4 μl of 2 mM dNTPs: 4 μl of 10×PCR buffer: 4 μl of 25 mM MgCl$_2$; 1 μl of the desired second round ASIN primer (10 pmol per μl); 1 μl of EK10R primer (10 pmol per μl): and 26 μl of MilliQ water. The following second round ASIN primers were used: CTAG-TA (5'-gggcacgattcgataacta-3': SEQ ID No. 5) (FIG. 4: lane 1) and CTAG-GC (5'-gggcacgattcgataacgc-3': SEQ ID No. 6) (FIG. 4: lane 3). The second round PCR mixes were added to the first round ASIN reactions and subjected to 25 cycles of: 95° C. for 10 s. 50° C. for 20 s. 72° C. for 60 s.

6 μl of each ASIN PCR amplification were run on a 2% agarose gel in 1×TAE buffer (40 mM Tris-Acetate, 1 mM EDTA) at 40V for 1 h. The gel was stained with ethidium before being photographed under UV transillumination.

EXAMPLE 2

ASIN PCR #1

PCR amplifications of region of the E. coli, fusA gene (SEQ ID No. 7) cloned on the pUC19 plasmid (plasmid pUC4G; J. Bacteriol. 176: 123–29) were performed using the ASIN procedure. First round ASIN PCR amplifications contained: 2.5 μl of 2 mM dNTPs: 2.5 μl of 10×PCR buffer [500 mM KCl, 100 mM Tris-HCl (pH 9.0 at 25° C.), 1% TritonX-100]; 2.5 μl of 25 mM MgCl$_2$; 1 μl of either of the two forward first round ASIN primers, 4G1 (5'-gat tcgataacnnnctgcaa-3': SEQ ID No. 8) or 4G3 (5'-gattcgataacnnntgagcg-3': SEQ ID No. 9) (10 pmol per μl): 1 μl of the reverse first round ASIN primer 4G6 (5'-gattcgataacnnntgacca-3': SEQ ID No. 10) (10 pmol per μl): 1 μl of the pUC4G template DNA (FIG. 5) (5 ng per μl).

The PCR reactions were preheated to 80° C. in a PE 2400 PCR machine and 5 μl of MilliQ water added containing 1 unit of Taq DNA polymerase. The reaction was subjected to 5 cycles of: 95° C. for 10 s, 39° C. for 1 min, 72° C. for 2 min. The PCR reaction was immediately subjected to a further 10 cycles of: 95° C. for 10 s, 54° C. for 30 s. 72° C. for 2 min.

Figure 6:
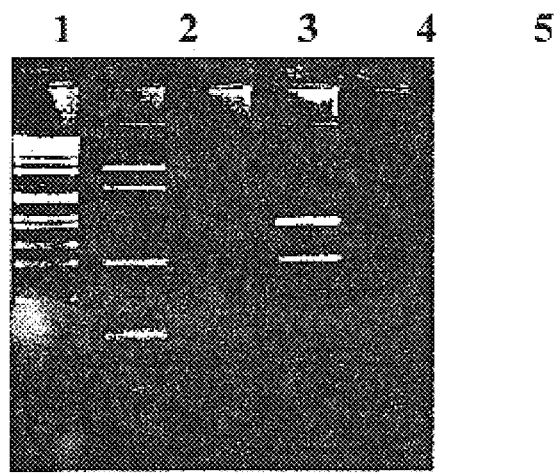
FIG. 6. fusA ASIN PCR and control reactions. Lane 1: 150 ng of Sppl/EcoRI DNA marker (8557, 7427, 6106, 4899, 3639, 2799, 1953, 1882, 1515, 1412, 1164, 992, 710, 492, 359.81 bp) Lane 2: 7 μl of the control ASIN PCR #1 amplification using primers 4G3 and 4G6. Lane 3: 3 μl of the ASIN PCR #2 product using primers 4G9 and 4G12. Lane 4: 7 μl of the control ASIN PCR #1 amplification using primers 4G 1 and 4G6. Lane 5: 1 μl of the ASIN PCR #2 product using primers 4G7 and 4G12.

Control ASIN PCR #1 reactions were performed as described previously except the PCR conditions were modified so that the final 10 cycles of: 95° C. for 10 s. 54° C. for 30 s, 72° C. for 2 min were changed to 25 cycles of: 95° C. for 10 s. 54° C. for 30 s, 72° C. for 2 min (FIG. 6: lanes 2 & 4).

ASIN PCR #2

The second round ASIN PCR mixes contained: 2.5 μl of 2 mM dNTPs: 2.5 μl of 10×PCR buffer: 2.5 μl of 25 mM MgCl$_2$: 1 μl of the desired second round ASIN primer (10 pmol per μl); and 10.5 μl of MilliQ water. The following second round ASIN primers were used: 4G12 (5'-gggcacgattcgataactac-3': SEQ ID No. 11) and 4G9 (5'-ggcacgattcgataacacg-3': SEQ ID No. 12) with the 4G3/4G6 ASIN PCR #1 reaction (FIG. 6: lane 3); 4G12 (5'-gggcacgattcgataactac-3') and 4G7 (5'-ggcacgattcgataacgcg-3': SEQ ID No. 13) with the 4G1/4G6 ASIN PCR #1 (FIG. 6; lane 5). 1 μl of the appropriate ASIN PCR #1 product was added to the second round ASIN reactions as template DNA.

The PCR reaction was preheated to 80° C. in a PE 2400 PCR machine and 5 μl of MilliQ water added containing 1 unit of Taq DNA polymerase. The reaction was subjected to 28 cycles of: 95° C. for 10 s. 47° C. for 30 s. 72° C. for 2 min.

5 μl of each ASIN PCR amplification were run on a 2% agarose gel in 1×TAE buffer (40 mM Tris-Acetate, 1 mM EDTA) at 70V for 40 min. The gel was stained with ethidium bromide before being photographed under UV transillumination.

EXAMPLE 3

The amplification of the target DNA using lambda DNA as a template. The nucleotide sequences of ASIN 1st and ASIN 2nd oligomers to amplify the target DNAs were shown in Table 1.

TABLE 1

| Target No. | ASIN 1st oliogomer | ASIN 2nd oliogomer |
|---|---|---|
| 1 | CACACAGGAAACAGCTATGACNNNCGCTAC (SEQ ID NO. 14) | CACACAGGAAACAGCTATGACCTT (SEQ ID NO. 17) |
| 2 | CACACAGGAAACAGCTATGACNNNCGATTT (SEQ ID NO. 15) | CACACAGGAAACAGCTATGACGGT (SEQ ID NO. 18) |
|  | CACACAGGAAACAGCTATGACNNNAACGCA (SEQ ID NO. 16) | CACACAGGAAACAGCTATGACGGT (SEQ ID NO. 19) |

The first reaction was carried out in 10 μL of reaction mixture containing Taq buffer (Takara Shuzo Co. Ltd.), 0.2 mM of dNTP, 2.5 ng of lambda DNA (Takara Shuzo Co. Ltd), one pmol of ASIN 1st oligomer, and one unit of Taq DNA polymerase (Takara Shuzo Co. Ltd.), for the first one cycle at 95° C. for 30 seconds followed by two cycles of 95° C. for ten seconds: 35° C. for one minute; and 72° C. for three minutes. Next, 40 μL of PCR mixture containing Taq buffer, 0.2 mM of dNTP, 10 pmol of ASIN 2nd oligomer, and 10 pmol of reverse primer (GTCGATAAATGGGCAATAC GAAC: SEQ ID No. 20) was added to the reaction solution. PCR was performed for 30 cycles of 95° C. for ten seconds; 55° C. for one minute; and 72° C. for three minutes. The amplified product was further purified by using Microcon YM-100(Takara Shuzo Co. Ltd.) to remove excess primer. The nucleotide sequence of purified product was determined by direct cycle sequencing using M13 RV primer (CAGGAAACAGCTATGAC: SEQ ID No. 21). With respect to target No.1, No.2, and No.3, 0.6 kb. 0.4 kb, and 1.7 kb of amplified products were obtained respectively, and the identified nucleotide sequence of these amplified products approximately 0.4 kb, was identical to that of target DNAs, which had been reported by Sanger et al. in *Journal of Molecular Biology*, 162, 729–773 (1982).

EXAMPLE 4

ASIN PCR#1

PCR amplifications of region of the *E. coli* fusA gene cloned on the pUC19 plasmid (plasmid pUC4G; *J. Bacteriol.* 176: 123–129) were performed using the ASIN procedure. First round ASIN PCR amplifications contained; 2.5 μl of 2 mM dNTPs; 2.5 μl of 10× PCR buffer [500 mM KCl, 100 mM Tris-HCl (pH 9.0 at 25° C.), 1% TritonX-100]; 2.5 μl of 25 mM MgCl$_2$; 1 μl of either of the two forward first round ASIN primers, 4G1 (5'-gattegataacnnnetgeaa-3') or 4G3 (5'-gattegataacnnnntgageg-3') (10 pmol per μl); 1 μl of the reverse first round ASIN primer 4G6 (5'-gattegataacnnnntgacca-3') (10 pmol per μl);1 μl of the pUC4G template DNA (5 ng per μl).

The PCR reactions were preheated to 80° C. in a PE 2400 PCR machine and 5 μl of MilliQ water added containing 1 unit of Taq DNA polymerase. The reaction was subjected to 5 cycles of: 95° C. for 10 s, 39° C. for 1 min. 72° C. for 2 min. The PCR reaction was immediately subjected to a further 25 cycles of: 95° C. for 10 s. 54° C. for 30 s. 72° C. for 2 min.

DNA sequencing

DNA sequencing reactions were performed using the mixed template products resulting from 4G1/4G6 (T1) and 4G3/4G6 (T2) amplifications. Excess primer was removed from T1 and T2 by ethanol precipitation. To 20 μl of each PCR product 2 μl of 3 M sodium acetate (pH 5.2) and 22 μl of 85% ethanol was added. The samples were incubated at room temperature for 5 min before centrifugation at 12000 g for 5 min. The supernatant was removed from the DNA pellets which were allowed to air dry for 30 min and dissolved in 8 μl of water.

DNA sequencing reactions were performed using: 4 μl of BigDye Terminator RR mix (ABI, Foster City, Calif.); 0.5 μl of either 4G7 (5'-ggcacgattegataacgeg-3') with template T1, or 4G9 (5'-ggcacgattegataacacg-3') with template T2: 3 μl of either T1 or T2 DNA templates: and 2.5 μl of milliQ water. The sequencing reactions were subjected to 25 cycles of: 95° C. for 10 s. 45° C. for 20 s. and 60° C. for 4 min. The sequencing reactions were purified using n-butanol (Biotechniques 26; 606–610) before analysis on ABI 377 DNA sequencer. The resulting DNA sequence data matched that previously obtained from the pUC4G plasmid.

EXAMPLE 5

Sequencing of a microbial genome

The ASIN primer walking approach is applied to sequencing a complete microbial genome as follows: Total DNA is extracted from a culture of the microorganism and three bacterial artificial chromosomal (BAC) libraries constructed, containing inserts of an average size of 1.3 Kbp. 5 Kbp, and 50–100 Kbp. The use of the low copy number BAC vector offers a number of advantages over the more standard cosmid and M13 based vectors, including: (1) the stable maintenance of the cloned inserts, thus avoiding analysis problems caused by gene re-arrangements or deletions; and (2) the gene libraries are more representative, as the problems associated with toxic or other unclonable sequences are reduced. In addition, the use of one vector system enables the use of standard cloning and host cultivation procedures.

Cloned inserts are obtained from the 1.3 Kbp and 5 Kbp BAC libraries by direct colony PCR (13). Specifically, colonies are picked directly from the agar plates and placed into individual wells of a 96-well PCR microtitre plate. The cloned inserts are then PCR amplified using two BAC vector-specific primers. This approach of colony PCR amplification has three major advantages: (1) the cost and effort of plasmid minipreps are avoided, (2) small insert BAC libraries can be used without the need to grow large volumes of host-cell culture, and (3) it provides a template that can be sequenced directly without further purification (28). The direct sequencing of unpurified PCR product requires that the concentration of the vector primers be adjusted to a level at which they are exhausted in the amplification process but without affecting the product yield.

Dye-terminator sequencing is performed using an initial shotgun phase on the 1.3 Kbp and 5 Kbp inserts to a level of one times genome coverage (approximately 2000 sequencing reactions per 1 Mbp), using the vector-specific primers used in the colony PCR amplification. This provides a large portion of the genome with little sequence redundancy. The ASIN primer walking strategy is then performed to obtain the remaining genomic sequence. The sequence fragments are assembled with the commercially available Sequencher sequence assembly and editing program, as described by Deckert and coworkers (7). Gaps between contigs are closed by sequencing approximately 200 randomly selected large insert clones from the 50–100 Kbp BAC library using either standard procedures or the ASIN approach. These sequences provide a scaffold to order the contigs and thus obtain the remaining unknown sequence. The complete sequence is then annotated and coding regions assigned using available computer programs(7.9).

EXAMPLE 6

A universal reverse genetics primer library

In a situation where, for example, the nucleotide sequence is not known but at least 3 amino acids of a peptide or protein sequence is known, the ASIN procedure can be used to obtain the peptide or protein sequence from template DNA encoding the protein.

Thus, the ASIN procedure may be used as a universal reverse genetics primer library. This requires, for example, the design of a modified version of the first degenerate 5' tagged nonamer library exemplified above. This primer library contains a common 5' tag sequence and complete degeneracy at positions 7, 8, and 9 from the 3' end. Positions 1 to 6 from the 3' end, however, would consist of two degenerate amino acid condons. In other words, each primer 3' end would encode for two degenerate amino acids. For example, the primer for the amino acids Glu-Leu-Asp would have the sequence 5' Tag—NNN CTN GA(T/C). This reverse genetics nonamer library would have about 400 members, that is, it would include every possible two amino acid combination. PCR amplification and sequencing is performed according to the ASIN procedure using suitable reverse primers. It will be clear to the skilled addressee that two sets of degenerate nonamer and triplet primers could be used when part of the amino acid sequence at the 3' end of the gene encoding the peptide or protein is known.

It will also be clear to the skilled addressee that this procedure will be more convenient when one of the amino acids is encoded by only one codon eg. met or trp.

Further, additional specificity for a particular peptide or protein sequence could be obtained by performing multiple nested amplification reactions using embedded sets of ASIN primers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Blocker. H., and D. N. Lincoln, 1994. The 'shortmer' approach to nucleic acid sequence analysis 1: computer simulation of sequencing projects to find economical primer sets. CABIOS. 10:193–197.
2. Bock, J. H., and J. L. Slightom, 1995. Fluorescence-based cycle sequencing with primers selected from a nonamer library. Bio Techniques. 19:60–64.
3. Bult, C. J., O. White, G. J. Olsen, et al. 1996. Complete genome sequence of the methanogenic archaeon, *Methanococcus jannaschii*. Science, 273:1058–1072.
4. Burbelo, P. D., and M. J. Iadarola, 1994. Rapid plasmid sequencing with multiple octamer primers, Bio Techniques. 16:645–650.
5. Cole, S. T., R. Brosch, J. Parkhill, et al. 1998. Deciphering the biology of *Mycobacterium tuberculosis* from the complete genome sequence. Nature. 393:537–542.
6. The *C. elegans* sequencing consortium. 1998. Genome sequence of the nematode *C. elegans*: A platform for investigation biology. Science.
7. Deckert, G., P. V. Warren, T. Gaasterland, et al. 1998. The complete genome of the hyperthermophilic bacteriom *Aquifex aeolicus*. Nature. 392:353–358.
8. Dunn, J. J., L. L. Butler-Loffredo, and F. W. Studier, 1995. Ligation of hexamers on hexamer templates to produce primers for cycle sequencing or the polymerase chain reaction. Anal. Biochem. 228:91–100.
9. Fleischmann, R. D., M. D. Adams, O. White, and e. al. 1995. Whole-genome random sequencing and assembly of *Haemophilus influenzae*. Science, 269:496–512.
10. Frazer, C. M., J. D. Gocayne, O. White, et al. 1995. The minimal gene complement of *Mycoplasma genitalium*. Science, 270:397–403.
11. Goffeau, A., et al. 1997. The yeast genome directory. Nature, 387 (Suppl):5–105.
12. Hardin, S. H., L. B. Jones, R. Homayouni, and J. C. McCollum. 1996. Octamer-primed cycle sequencing: Design of an optimized primer library. Genome Res. 6:545–550.
13. Hofmann, M. A., and D. A. Brian, 1991. Sequencing PCR DNA amplified directly from a bacterial colony. Bio Techniques. 11:30–31.
14. Jones, L. B., and S. H. Hardin. 1998. Octamer-primed cycle sequencing using dye-terminator chemistry, Nucleic Acids Res. 26:2824–2826.
15. Kaczorowski, T., and W. Szybalski, 1994. Assembly of a 18-nucleotide primers by ligation of three hexamers: sequencing of large genomes by primer walking. Anal. Biochem. 221:127–135.
16. Kaczorowski, T., and W. Szybalski. 1996. Automated four-color DNA sequencing using primers assembled by hexamer ligation. Gene. 179:195–198.
17. Kaczorowski, T., and W. Szybalski. 1996. Co-operativity of hexamer ligation. Gene. 179:189–193.
18. Kaczorowski, T., and W. Szybalski. 1998. Genomic DNA sequencing by SPEL-6 primer walking using hexamer ligation. Gene. 223:83–91.
19. Kaczorowski, T., and W. Szybalski. 1993. Sequencing by primer assembly (from a library of hexamers) and primer walking. Gene. 135:286–290.
20. Kaneko, T., S. Sato, H. Katoni, et al. 1996. *Synechocystis sp*. Strain PCC6803. II. Sequence determination of the entire genome and assignment of potential protein-coding regions. DNA Res. 3:109–136.
21. Kieleczawa, J., J. J. Dunn, and F. W. Studier. 1992. DNA sequencing by primer walking with strings of contiguous hexamer ligation. Science. 258:1787–1791.
22. Kolter, L. E., D. Zevin-Sonkin, I. A. Sobelev, A. D. Beskin, and L. E. Ulanovsky. 1993. DNA sequencing: modular primers assembled from a library of hexamers and pentamers. Proc. Natl. Acad. Sci. USA. 90:4241–4345.
23. Rychlik, W. 1995. Priming efficiency in PCR, Bio Techniques. 18:84–90.

24. Siemieniak, D. R., and J. L. Slightom. 1990. A library of 3342 useful nonamer primers for genome sequencing. Gene. 96:121–124.
25. Strauss, E. C., J. A. Kobori, G. Siu, and L. E. Hood. 1986. Specific-primer-directed DNA sequencing, Anal. Biochem. 154:353–360.
26. Studier, F. W. 1989. A strategy for high-volume sequencing of cosimd DNAs: Random and directed priming with a library of oligonucleotides. Proc. Natl. Acad. Sci. USA. 86:6917–6921.
27. Szybalski, W. 1990. Proposal for sequencing DNA using ligation of hexamers to generate sequential elongation primers (SPEL-6). Gene. 90:177–178.
28. Trower, M. K., D. Burt, I. J. Puvis, C. W. Dykes, and C. Christodoulou. 1995. Fluorescent dye-primer cycle sequencing using unpurified PCR products as templates; development of a protocol amenable to high-throughput DNA sequencing. Nucleic Acids Res. 23:2348–2349.
29. Venter, J. C., H. O. Smith, and L. Hood. 1996. A new strategy for genome sequencing. Nature. 381:364–366.

What is claimed is:

1. A method of amplifying a nucleotide sequence of interest wherein the nucleotide sequence comprises at least one region of known sequence, wherein the region of known sequence comprises, in a 3' to 5' direction: a first known region and a second known region wherein the first and second known regions are immediately adjacent each other and wherein the method comprises:

1) a first amplification step of at least two cycles comprising amplifying the nucleotide sequence of interest using at least
   (a) as a template, a sequence comprising at least the nucleotide sequence of interest;
   (b) one first primer having, in a 5' to 3' direction: a 5' tag sequence; a degenerate sequence corresponding to the first known region; and a sequence complementary to the second known region of the nucleotide sequence of interest; and
   (c) a reverse primer, deoxyribonucleoside triphosphates (dNTPs) and suitable enzyme conducted under reaction conditions such that the first amplification step generates a first amplification product; and 2) a second amplification step comprising amplifying the nucleotide sequence of interest using at least
   (a) as a template, the first amplification product; and
   (b) one second primer having, in a 5' to 3' direction: a sequence which hybridises to the complementary strand of the 5' tag sequence of the first primer and a sequence complementary to the first known region of the nucleotide sequence of interest; which second amplification step generates a second amplification product.

2. A method of amplifying and sequencing a nucleotide sequence of interest comprising amplifying a nucleotide sequence of interest according to the method of claim 1 and sequencing the second amplification product.

3. A method according to claim 1 wherein the amplification step is a polymerase chain reaction.

4. A method according to claim 1 wherein, in the first and second primers respectively, the 5' tag sequence and the sequence which hybridises to the complementary strand of the 5' tag sequence of the first primer, are the same.

5. A method according to claim 1 wherein the 5' tag sequence is a vector specific sequence.

6. A method according to claim 5 wherein the 5' tag sequence is derived from M13 phage, pUC18, pBR322, pGEM, BLUESCRIPT, or pBELOBACII.

7. A method according to claim 1 wherein the 5' tag sequence is 10 to 25 bases in length.

8. A method according to claim 7 wherein the 5' tag sequence is 15 to 18 bases in length.

9. A method according to claim 8 wherein the 5' tag sequence is 15 bases in length.

10. A method according to claim 1 wherein, in the first primer, the sequence complementary to the second known region is 4 to 8 bases in length.

11. A method according to claim 10 wherein, in the first primer, the sequence complementary to the second known region is 6 bases in length.

12. A method according to claim 1 wherein, in the first primer, the degenerate sequence together with the sequence complementary to the second known region of the nucleotide sequence of interest is 6 to 12 bases in length.

13. A method according to claim 12 wherein, in the first primer, the degenerate sequence together with the sequence complementary to the second known region of the nucleotide sequence of interest is 9 bases in length.

14. A method according to claim 1 wherein, in the second primer, the sequence complementary to the first known region of the nucleotide sequence of interest is 1 to 5 bases in length.

15. A method according to claim 14 wherein, in the second primer, the sequence complementary to the first known region of the nucleotide sequence of interest is 3 bases in length.

16. A method according to claim 2 wherein the 5' tag sequence, or a sequence which hybridises to the complementary sequence of the 5' tag sequence, is used as a sequencing primer.

17. A method according to claim 2 wherein the second primer is used as a sequencing primer.

18. A method according to claim 1 wherein the first and second amplifications comprise two first primers and two second primers respectively, wherein one of the first primers acts as a reverse primer in the first amplification step and one of the second primers acts as a reverse primer in the second amplification step.

19. A method according to claim 18 wherein the 5' tag sequence on each of the first primers is different.

20. A method according to claim 1 wherein steps 1) and 2) are performed simultaneously.

21. A set of primers comprising:
(a) a first primer having, in a 5' to 3' direction: a 5' tag sequence; a degenerate sequence; and a predetermined sequence, wherein the sequences are immediately adjacent to each other; and
(b) a second primer having in a 5' to 3' direction: a sequence which hybridises to the complementary strand of the 5' tag sequence of the first primer, and a predetermined sequence corresponding to at least a portion of the degenerate sequence of the first primer.

22. A primer set according to claim 21 wherein, the predetermined sequence of the first primer is 4 to 8 bases in length.

23. A primer set according to claim 22 wherein, the predetermined sequence of the first primer is 6 bases in length.

24. A primer set according to claim 21 wherein, the degenerate sequence together with the predetermined sequence of the first primer is 6 to 12 bases in length.

25. A primer set according to claim 24 wherein, the degenerate sequence together with the predetermined sequence of the first primer is 9 bases in length.

26. A primer set according to claim 21 wherein, the predetermined sequence of the second primer is 1 to 5 bases in length.

27. A primer set according to claim 26 wherein, the predetermined sequence of the second primer is 3 bases in length.

28. A primer set according to claim 21 wherein the 5' tag sequence is a vector specific sequence.

29. A primer set according to claim 28 wherein the 5' tag sequence is derived from M13 phage, pUC18, pBR322, pGEM, BLUESCRIPT, or pBELOBACII.

30. A primer set according to claim 21 wherein the 5' tag sequence is 10 to 25 bases in length.

31. A primer set according to claim 30 wherein the 5' tag sequence is 15 to 18 bases in length.

32. A primer set according to claim 31 wherein the 5' tag sequence is 15 bases in length.

33. A primer set library comprising a set of primers according to claim 21.

34. A kit comprising a primer set according to claim 21.

35. A kit comprising a primer library according to claim 33.

36. A method of amplifying and sequencing a nucleotide sequence of interest wherein the nucleotide sequence comprises at least one region of known sequence, wherein the region of known sequence comprises, in a 3' to 5' direction: a first known region of 3 bases and a second known region of 6 bases wherein the first and second known regions are immediately adjacent each other and wherein the method comprises:
1) a first polymerase chain reaction (PCR) of at least two cycles comprising at least
   (a) as a template, a sequence comprising at least the nucleotide sequence of interest;
   (b) one first primer having, in a 5' to 3' direction: a 5' tag sequence; a degenerate sequence corresponding to the first known region; and a sequence complementary to the second known region of the nucleotide sequence of interest; and
   (c) a reverse primer, deoxyribonucleoside triphosphates (dNTPs) and polymerase conducted under reaction conditions such that the first PCR generates a first PCR product;
2) a second PCR comprising at least
   (a) as a template, the first PCR product; and
   (b) one second primer having, in a 5' to 3' direction: the same 5' tag sequence as the first primer and a sequence complementary to the first known region of the nucleotide sequence of interest which second PCR generates a second PCR product; and
3) sequencing the second PCR product using the 5' tag sequence as a sequencing primer.

37. A method of amplifying and sequencing a nucleotide sequence of interest wherein the nucleotide sequence comprises at least one region of known sequence, wherein the region of known sequence comprises, in a 3' to 5' direction: a first known region and a second known region wherein the first and second known regions are immediately adjacent each other and wherein the method comprises:

1) an amplification step of at least two cycles comprising amplifying the nucleotide sequence of interest using at least
   (a) as a template, a sequence comprising at least the nucleotide sequence of interest:
   (b) one primer having, in a 5' to 3' direction: a 5' tag sequence; a degenerate sequence corresponding to the first known region; and a sequence complementary to the second known region of the nucleotide sequence of interest; and
   (c) a reverse primer, deoxyribonucleoside triphosphates (dNTPs) and suitable enzyme under reaction conditions such that the amplification step generates an amplification product; and
2) a sequencing step comprising sequencing the amplification product using:
   (a) as a template, the amplification product; and a sequencing primer having, in a 5' to 3' direction; a sequence which hybridises to the complementary strand of the 5' tag sequence of the primer utilised in the amplification step, and a sequence complementary to the first known region of the nucleotide sequence of interest.

38. A method according to claim 37 wherein the amplification step is a polymerase chain reaction.

39. A method according to claim 37 wherein, in the primer utilised in the amplification step and in the sequencing primers respectively, the 5' tag sequence and the sequence which hybridises to the complementary strand of the 5' tag sequence of the primer utilised in the amplification step, and the same.

40. A method according to claim 36 wherein the 5' tag sequence is a vector specific sequence.

41. A method according to claim 39 wherein the 5' tag sequence is derived from M13 phage, pUC18, pBR322, pGEM, BLUESCRIPT, or pBELOBACII.

42. A method according to claim 36 wherein the 5' tag sequence is 10 to 25 bases in length.

43. A method according to claim 42 wherein the 5' tag sequence is 15 to 18 bases in length.

44. A method according to claim 43 wherein the 5' tag sequence is 15 bases in length.

45. A method according to claim 37 wherein, in the primer utilised in the amplification step, the sequence complementary to the second known region is 4 to 8 bases in length.

46. A method according to claim 45 wherein, in the primer utilised in the amplification step, the sequence complementary to the second known region is 6 bases in length.

47. A method according to claim 37 wherein, in the primer utilised in the amplification step, the degenerate sequence together with the sequence complementary to the second known region of the nucleotide sequence of interest is 6 to 12 bases in length.

48. A method according to claim 47 wherein, in the primer utilised in the amplification step, the degenerate sequence together with the sequence complementary to the second known region of the nucleotide sequence of interest is 9 bases in length.

49. A method according to claim 38 wherein, in the sequencing primer, the sequence complementary to the first known region of the nucleotide sequence of interest is 1 to 5 bases in length.

50. A method according to claim 49 wherein, in the sequencing primer, the sequence complementary to the first known region of the nucleotide sequence of interest is 3 bases in length.

* * * * *